(12) United States Patent
Itou

(10) Patent No.: US 9,340,516 B2
(45) Date of Patent: May 17, 2016

(54) FORM-II CRYSTAL OF 2-{4-[N-(5,6-DIPHENYLPYRAZIN-2-YL)-N-ISOPROPYLAMINO]BUTYLOXY}-N-(METHYLSULFONYL) ACETAMIDE, METHOD FOR PRODUCING THE SAME, AND USE THEREOF

(71) Applicant: Hideyuki Itou, Kyoto (JP)

(72) Inventor: Hideyuki Itou, Kyoto (JP)

(73) Assignee: NIPPON SHINYAKU COMPANY, LTD., Kyoto (JP)

( * ) Notice: Subject to any disclaimer, the term of this patent is extended or adjusted under 35 U.S.C. 154(b) by 0 days.

(21) Appl. No.: 14/160,699

(22) Filed: Jan. 22, 2014

(65) Prior Publication Data

US 2014/0155414 A1    Jun. 5, 2014

Related U.S. Application Data

(62) Division of application No. 13/379,531, filed as application No. PCT/JP2010/060798 on Jun. 25, 2010, now Pat. No. 8,791,122.

(30) Foreign Application Priority Data

Jun. 26, 2009 (JP) ................. 2009-151727
Jun. 26, 2009 (JP) ................. 2009-151728
Jun. 26, 2009 (JP) ................. 2009-151729

(51) Int. Cl.
*C07D 241/20* (2006.01)
*A61K 31/4965* (2006.01)

(52) U.S. Cl.
CPC .......... *C07D 241/20* (2013.01); *A61K 31/4965* (2013.01)

(58) Field of Classification Search
CPC ......................... C07D 241/20; A61K 31/4965
See application file for complete search history.

(56) References Cited

U.S. PATENT DOCUMENTS

| | | | |
|---|---|---|---|
| 8,394,793 B2 | 3/2013 | Kyoi | |
| 8,575,175 B2 | 11/2013 | Matsuda et al. | |
| 8,629,145 B2 | 1/2014 | Kuwano | |
| 8,729,086 B2 | 5/2014 | Murakami et al. | |
| 8,889,693 B2 | 11/2014 | Murakami et al. | |
| 2003/0092760 A1 | 5/2003 | Kurumatani et al. | |
| 2004/0102436 A1 | 5/2004 | Asaki et al. | |
| 2004/0116530 A1 | 6/2004 | Maeda et al. | |
| 2006/0189695 A1 | 8/2006 | Uchida et al. | |
| 2011/0015211 A1 | 1/2011 | Murakami et al. | |
| 2011/0098481 A1 | 4/2011 | Murata et al. | |
| 2011/0105518 A1 | 5/2011 | Kuwano | |
| 2011/0118254 A1 | 5/2011 | Kyoi | |
| 2011/0178103 A1 | 7/2011 | Matsuda et al. | |
| 2014/0221397 A1 | 8/2014 | Murakami et al | |

FOREIGN PATENT DOCUMENTS

| | | |
|---|---|---|
| EP | 1 106 176 A1 | 6/2001 |
| EP | 1400518 A1 | 3/2004 |
| EP | 1 642 584 A1 | 4/2006 |
| EP | 2 246 336 A1 | 11/2010 |
| EP | 2 289 518 A1 | 3/2011 |
| EP | 2 292 231 A1 | 3/2011 |
| EP | 2 343 292 A1 | 7/2011 |
| WO | 02/088084 A1 | 11/2002 |
| WO | 2009/107736 A1 | 9/2009 |
| WO | 2009/154246 A1 | 12/2009 |
| WO | 2009/157396 A1 | 12/2009 |
| WO | 2009/157397 A1 | 12/2009 |
| WO | 2009/157398 A1 | 12/2009 |

OTHER PUBLICATIONS

J. Keith Guillory, "Generation of Polymorphs, Hydrates, Solvates, and Amorphous Solids," Polymorphism in Pharmaceutical Solids, pp. 183-226, Marcel Dekker, Inc., New York (1999).
Mino R. Caira, "Crystalline Polymorphism of Organic Compounds," Topics in Current Chemistry, vol. 198, pp. 163-208 (1998).
Vippagunta, et al., "Crystalline Solids," Advanced Drug Delivery Reviews, vol. 48, pp. 3-26, (2001).
Morissette, et al., "High-Throughput Crystallization: Polymorphs, Salts, Co-Crystals and Solvates of Pharmaceutical Solids," Advanced Drug Delivery Reviews, vol. 56, pp. 275-300, (2004).
Byrn, et al., "Pharmaceutical Solids: A Strategic Approach to Regulatory Considerations," Pharmaceutical Research, vol. 12, No. 7, pp. 945-954 (1995).
David J.W. Grant, "Theory and Origin of Polymorphism," Polymorphism in Pharmaceutical Solids, pp. 1-10, Marcel Dekker, Inc., New York (1999).
Gennaro, "Remington: The Science and Practice of Pharmacy," 19th Edition, Second Volume, Lippincott Williams & Wilkins, (1995).

(Continued)

*Primary Examiner* — Rebecca Anderson
*Assistant Examiner* — Karen Cheng

(57) ABSTRACT

Form-II crystal of 2-{4-[N-(5,6-diphenylpyrazin-2-yl)-N-isopropylamino]butyloxy}-N-(methylsulfonyl)acetamide and a method of producing the crystal are provided. The Form-II crystal exhibits diffraction peaks in its X-ray powder diffraction spectrum at least at the following angles of diffraction 2θ when the spectrum is obtained by using Cu Kα radiation: 9.0 degrees, 12.9 degrees, 20.7 degrees, and 22.6 degrees. The Form-II crystal can be produced by crystallizing the subject compound from an alcoholic solvent, a ketone solvent, a saturated hydrocarbon solvent, an ether solvent, water, or a mixture of these solvents. The crystal may be administered as an active ingredient to a subject for the purpose of treating or preventing certain diseases, disorders, and symptoms, or for promoting angiogenesis or gene therapy. The targeted diseases and disorders include transient ischemic attack, diabetic neuropathy, diabetic gangrene, peripheral circulatory disturbance, connective tissue disease, reocclusion/restenosis after percutaneous transluminal coronary angioplasty, arteriosclerosis, thrombosis, hypertension, pulmonary hypertension, and diabetic nephropathy.

11 Claims, 6 Drawing Sheets

(56) References Cited

OTHER PUBLICATIONS

The International Bureau of WIPO, International Preliminary Report on Patentability Issued in PCT/JP2010/060798 on Jan. 17, 2012.
Asaki et al., 2007, Bioorganic & Medicinal Chemistry, vol. 15, p. 6692-6704.
Gelim et al., Current Atherosclerosis Reports, 2009, vol. 11, p. 227-235.
Yin, Hepatology, 2007, vol. 45, No. 1, p. 159-169.
Zhou et al., 2012, vol. 7, Issue 5, PLOS, p. 1-12.
Tatsuya Atsumi et al., "Improvement of skin temperature of fingers by beraprost sodium in patients with Raynaud's phenomenon", Japanese Journal of Clinical Immunology, vol. 16 (5), pp. 409-414 (1993).
David B. Badesch et al., "Longterm Survival Among Patients with Scleroderma-associated Pulmonary Arterial Hypertension Treated with Intravenous Epoprostenol", The Journal of Rheumatology, vol. 36 (10), pp. 2244-2249 (2009).
Robyn J. Barst, M.D., et al., "A Comparison of Continuous Intravenous Epoprostenol (Prostacyclin) with Conventional Therapy for Primary Pulmonary Hypertension", The New England Journal of Medicine, vol. 334, pp. 296-301 (Feb. 1, 1996).
G. Bergman et al., "Prostacyclin: Haemodynamic and Metabolic Effects in Patients with Coronary Artery Disease", The Lancet, vol. 14, pp. 569-572 (Mar. 14. 1981), The Lancet Ltd.
Yan Chen et al., "Protective effect of beraprost sodium, a stable prostacyclin analog, in the development of cigarette smoke extract-induced emphysema", American Journal of Physiology—Lung Cellular and Molecular Physiology, vol. 296, pp. L648-L656 (2009), the American Physiological Society.
P. Henriksson et al., "Prostacyclin infusion in patients with acute myocardial infarction", British Heart Journal, vol. 53, pp. 173-179 (1985).
Tetsuya Hirano et al., "Effect of Beraprost Sodium (TRK-100) on Erythrocyte Deformability, Blood Viscosity and Thrombus Formation in Rats", Japanese Journal of Thrombosis and Hemostasis, vol. 1:2, pp. 94-105 (1990).
Marco Idzko et al., "Inhaled iloprost suppresses the cardinal features of asthma via inhibition of airway dendritic cell function", The Journal of Clinical Investigation, vol. 177, No. 2, pp. 464-472 (Feb. 2007).
Keiichi Kuwano et al., "A Long-Acting and Highly Selective Prostacyclin Receptor Agonist Prodrug, 2-{4-[(5,6-Diphenylpyrazin-2-yl)(isopropyl)amino]butoxy}-N-(methylsulfonyl)acetamide (NS-304), Ameliorates Rat Pulmonary Hypertension with Unique Relaxant Responses of Its Active Form, {4-[(5,6-Diphenylpyrazin-2-yl)(isopropyl)amino]Butoxy}acetic Acid (MRE-269), on Rat Pulmonary Artery", The Journal of Pharmacology and Experimental Therapeutics, vol. 326, No. 3, pp. 691-699 (2008).
T. Matsumoto et al., "The efficacy of Oral Beraprost Sodium, a prostaglandin I2 analogue, for treating intermittent claudication in patients with arteriosclerosis obliterans", International Angiology, vol. 29, Suppl. 1 to No. 2, pp. 49-54 (Apr. 2010), Edizioni Minerva Medica.
Soichiro Mochio et al., "Effect of the PGI2 Analogue, Berapost Sodium (BPS), on Diabetic Neuropathy in Diabetic WBN/Kob Rats", Journal of the Japan Diabetes Society, vol. 36, No. 11, pp. 881-884 (1993), The Japan Diabetes Society,
Shintaro Nishio and Hajimu Kurumantani, "Pharmacological and clinical properties of berapost sodium, orally active prostacyclin analogue", Folia Pharmacologica Japonica, vol. 117, No. 2, pp. 123-130 (2001).
Teruhiko Umetsu et al., "Antithrombotic Effect of TRK-100, a Novel, Stable PGI2 Analogue", The Japanese Journal of Pharmacology, vol. 43, pp. 81-90 (1987), The Japanese Pharmacological Society.
M. Watanabe et al., "Amelioration of diabetic nephropathy in OLETF rats by prostaglandin I(2) analog, berapost sodium", American Journal of Nephrology, vol. 30, No. 1, pp. 1-11 (2009), Abstract, [online] <http://www.ncbi.nlm.nih.gov/pubmed/19158439>, retrieved Feb. 19, 2015.
Masateru Yamada et al., "Amelioration by beraprost sodium, a prostacyclin analogue, of established renal dysfunction in rat glomerulonephritis model", European Journal of Pharmacology, vol. 449, pp. 167-176 (2002), Elsevier B.V.
The State Intellectual Property Office of the People's Republic of China, "Notice of the First Office Action", received for Chinese Patent Application No. 201080028176.8, which is a Chinese national-stage application of PCT/JP2010/060798, from which the current U.S. application claims priority, mailed on Oct. 28, 2013, 13 pages (6 pages of English Translation of Notice of the First Office Action, 7 pages of Notice of the First Office Action).
Observation filed by Nippon Shinyaku Co., Ltd. in Chinese Patent Application No. 201080028176.8, which is a Chinese national-stage application of PCT/JP2010/060798, from which current U.S. application claims priority, submitted to the Chinese Patent Office on May 9, 2014, in response to the "Notice of the First Office Action"mailed on Oct. 28, 2013, 6 pages (3 pages of English Translation of Observation, 3 pages of Observation).
Response to Russian Office Action of Feb. 27, 2014, submitted in Russian Patent Application No. 2012102678, which is a Russian counterpart of the parent application (U.S. Appl. No. 13/379,531) of the present application.
Response to Russian Office Action of Feb. 27, 2014, submitted on Feb. 27, 2015, in Russian Patent Application No. 2012102678, which is a Russian counterpart of the parent application (U.S. Appl. No. 13/379,531) of the present application.
Nippon Shinyaku Co., Ltd., Demand for Trial for Japanese Patent Application No. 2011-519943, which is a Japanese counterpart of family of U.S. Appl. No. 14/160,699, submitted to Japan Patent Office on Apr. 9, 2015, 21 pages (13 pages of English Translation of Demand for Trial, 8 pages of Demand of Trial).
Nippon Shinyaku Co., Ltd., Recourse of Appeal for Columbian Patent Application No. 11 178426, which is a Columbian counterpart of family of U.S. Appl. No. 14/160,699, submitted to Superintendent of Industry and Trade on May 14, 2014, 21 pages (10 pages of English Translation of Recource of Appeal and 11 pages of Recourse of Appeal).
Nippon Shinyaku Co., Ltd., Appendix 1 to Recourse of Appeal for Columbian Patent Application No. 11 178426, which is a Columbian counterpart of family of U.S. Appl. No. 14/160,699, ICH Harmonised Tripartite Guideline, Impurities: Guideline for Residual Solvents Q3C(R5), Step 4 version dated Feb. 4, 2011, 29 pages.
Nippon Shinyaku Co., Ltd., Appendix 2 to Recourse of Appeal for Columbian Patent Application No. 11 178426, which is a columbian counterpart of family of U.S. Appl. No. 14/160,699, ICH Harmonised Tripartite Guideline, Impurities in New Drug Substances Q3A(R2), Step 4 version dated Oct. 25, 2006, 15 pages.
Nippon Shinyaku Co., Ltd., Appendix 4 to Recourse of Appeal for Columbian Patent Application No. 11 178426, which is a Columbian counterpart of family of U.S. Appl. No. 14/160,699, Descriptions of Experiments 1 and 2, 5 pages.
Nippon Shinyaku Co., Ltd., Recourse of Appeal for Columbian Patent Application No. 14 103656, which is a Divisional Application of Columbian Patent Application No. 11 178426 and a Columbian counterpart of family of U.S. Appl. No. 14/160,699, submitted to Superintendent of Industry and Trade on Nov. 6, 2014, 24 pages (13 pages of English Translation of Recource of Appeal and 11 pages of Recource of Appeal.
Nippon Shinyaku Co., Ltd., Appendix 2 to Recourse of Appeal for Columbian Patent Application No. 14 103656, which is a Divisional Application of Columbian Patent Application No. 11 178426 and a Columbian counterpart of family of U.S. Appl. No. 14/160,699, ICH Harmonised Tripartite Guideline, Impurities in New Drug Substances Q3A(R2), Step 4 version dated Oct. 25, 2006, 15 pages.
Nippon Shinyaku Co., Ltd., Reply to the Communication for European Patent Application No. 10 79 2183.5-1211, which is a European counterpart of family of U.S. Appl. No. 14/160,699, submitted to European Patent Office on Jun. 13, 2013, 4 pages.
Nippon Shinyaku Co., Ltd., Response to Office Action for Israeli Patent Application No. 216928, which is an Israeli counterpart of family of U.S. Appl. No. 14/160,699, submitted to Israel Patent Office on Jul. 3, 2014, 9 pages.

(56) References Cited

OTHER PUBLICATIONS

Nippon Shinyaku Co., Ltd., Appendix 1 to Response to Office Action for Israeli Patent Application No. 216928, which is an Israeli counterpart of family of U.S. Appl. No. 14/160,699, Powder X-ray diffraction spectra, 2 pages.

Nippon Shinyaku Co., Ltd., Appendix 2 to Response to Office Action for Israeli Patent Application No. 216928, which is an Israeli counterpart of family of U.S. Appl. No. 14/160,699, ICH Harmonised Tripartite Guideline, Impurities: Guideline for Residual Solvents Q3C(R5), Step 4 version dated Feb. 4, 2011, 29 pages.

Nippon Shinyaku Co., Ltd., Appendix 3 to Response to Office Action for Israeli Patent Application No. 216928, which is an Israeli counterpart of family of U.S. Appl. No. 14/160,699, ICH Harmonised Tripartite Guideline, Impurities in New Drug Substances Q3A(R2), Step 4 version dated Oct. 25, 2006, 15 pages.

Nippon Shinyaku Co., Ltd., Appendix 4 to Response to Office Action for Israeli Patent Application No. 216928, which is an Israeli counterpart of family of U.S. Appl. No. 14/160,699, Descriptions of Experiments 1 and 2, 5 pages.

Nippon Shinyaku Co., Ltd., Written Opinion for Japanese Patent Application No. 2011-519943, which is a Japanese Counterpart of family of U.S. Appl. No. 14/160,699, submitted to Japan Patent Office on Nov. 28, 2014, 17 pages (12 pages of English Translation of Written Opinion, 5 pages of Written Opinion).

Nippon Shinyaku Co., Ltd., Response to Office Action for Philippine Patent Application No. 1-2011-502567, which is a Philippine counterpart of family of U.S. Appl. No. 14/160,699, submitted to Intellectual Property Office of the Philippines on May 28, 2014, 5 pages.

Nippon Shinyaku Co., Ltd., Appendix 1 to Response to Office Action for Philippine Patent Application No. 1-2011-502567, which is a Philippine counterpart of family of U.S. Appl. No. 14/160,699, Powder X-ray diffraction spectra, 2 pages.

Nippon Shinyaku Co., Ltd., Appendix 2 to Response to Office Action for Philippine Patent Application No. 1-2011-502567, which is a Philippine counterpart of family of U.S. Appl. No. 14/160,699, ICH Harmonised Tripartite Guideline, Impurities: Guideline for Residual Solvents Q3C(R5), Step 4 version dated Feb. 4, 2011, 29 pages.

Nippon Shinyaku Co., Ltd., Appendix 3 to Response to Office Action for Philippine Patent Application No. 1-2011-502567, which is a Philippine counterpart of family of U.S. Appl. No. 14/160,699, ICH Harmonised Tripartite Guideline, Impurities in New Drug Substances Q3A(R2), Step 4 version dated Oct. 25, 2006, 15 pages.

Nippon Shinyaku Co., Ltd., Appendix 4 to Response to Office Action for Philippine Patent Application No. 1-2011-502567, which is a Philippine counterpart of family of U.S. Appl. No. 14/160,699, Descriptions of Experiments 1 and 2, 5 pages.

"Rational Polymorph Screening on NS-304: Final Report for Nippon Shinyaku," dated Dec. 2008.

FORM-II CRYSTAL OF 2-{4-[N-(5,6-DIPHENYLPYRAZIN-2-YL)-N-ISOPROPYLAMINO]BUTYLOXY}-N-(METHYLSULFONYL) ACETAMIDE, METHOD FOR PRODUCING THE SAME, AND USE THEREOF

CROSS-REFERENCE TO RELATED APPLICATIONS

This patent application is a divisional of U.S. application Ser. No. 13/379,531 filed on Dec. 20, 2011, now U.S. Pat. No. 8,791,122 B2, which is a U.S. national stage entry under 35 U.S.C. §371 of International Patent Application No. PCT/JP2010/060798 filed on Jun. 25, 2010, which claims the benefit of foreign priority to Japanese Patent Application Nos. JP 2009-151727, JP 2009-151728, and JP 2009-151729 each filed on Jun. 26, 2009. The U.S. application Ser. No. 13/379,531 was published on Apr. 26, 2012, as US 2012/0101276 A1. The International Application was published in Japanese on Dec. 29, 2010, as International Publication No. WO 2010/150865 A1 under PCT Article 21(2).

FIELD OF THE INVENTION

The present invention relates to a crystal of 2-{4-[N-(5,6-diphenylpyrazin-2-yl)-N-isopropylamino]butyloxy}-N-(methylsulfonyl)acetamide (hereinafter referred to as "compound A").

[Formula 1]

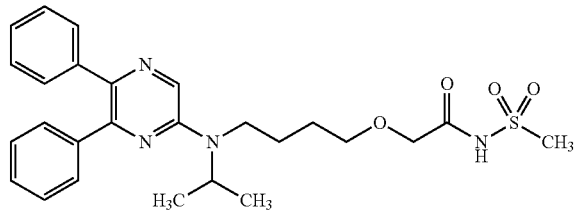

BACKGROUND OF THE INVENTION

Compound A has an excellent PGI2 agonistic effect and shows a platelet aggregation inhibitory effect, a vasodilative effect, a bronchodilative effect, a lipid deposition inhibitory effect, a leukocyte activation inhibitory effect, etc. (see, for example, in WO 2002/088084 ("WO '084")).

Specifically, compound A is useful as preventive or therapeutic agents for transient ischemic attack (TIA), diabetic neuropathy, diabetic gangrene, peripheral circulatory disturbance (e.g., chronic arterial occlusion, intermittent claudication, peripheral embolism, vibration syndrome, Raynaud's disease), connective tissue disease (e.g., systemic lupus erythematosus, scleroderma, mixed connective tissue disease, vasculitic syndrome), reocclusion/restenosis after percutaneous transluminal coronary angioplasty (PTCA), arteriosclerosis, thrombosis (e.g., acute-phase cerebral thrombosis, pulmonary embolism), hypertension, pulmonary hypertension, ischemic disorder (e.g., cerebral infarction, myocardial infarction), angina (e.g., stable angina, unstable angina), glomerulonephritis, diabetic nephropathy, chronic renal failure, allergy, bronchial asthma, ulcer, pressure ulcer (bedsore), restenosis after coronary intervention such as atherectomy and stent implantation, thrombocytopenia by dialysis, the diseases in which fibrosis of organs or tissues is involved [e.g., Renal diseases (e.g., tuburointerstitial nephritis), respiratory diseases (e.g., interstitial pneumonia (pulmonary fibrosis), chronic obstructive pulmonary disease), digestive diseases (e.g., hepatocirrhosis, viral hepatitis, chronic pancreatitis and scirrhous stomachic cancer), cardiovascular diseases (e.g, myocardial fibrosis), bone and articular diseases (e.g, bone marrow fibrosis and rheumatoid arthritis), skin diseases (e.g, cicatrix after operation, scalded cicatrix, keloid, and hypertrophic cicatrix), obstetric diseases (e.g., hysteromyoma), urinary diseases (e.g., prostatic hypertrophy), other diseases (e.g., Alzheimer's disease, sclerosing peritonitis, type I diabetes and organ adhesion after operation)], erectile dysfunction (e.g., diabetic erectile dysfunction, psychogenic erectile dysfunction, psychotic erectile dysfunction, erectile dysfunction associated with chronic renal failure, erectile dysfunction after intrapelvic operation for removing prostata, and vascular erectile dysfunction associated with aging and arteriosclerosis), inflammatory bowel disease (e.g., ulcerative colitis, Crohn's disease, intestinal tuberculosis, ischemic colitis and intestinal ulcer associated with Behcet disease), gastritis, gastric ulcer, ischemic ophthalmopathy (e.g., retinal artery occlusion, retinal vein occlusion, ischemic optic neuropathy), sudden hearing loss, avascular necrosis of bone, intestinal damage caused by administration of a non-steroidal anti-inflammatory agent (e.g., diclofenac, meloxicam, oxaprozin, nabumetone, indomethacin, ibuprofen, ketoprofen, naproxen, celecoxib) (there is no particular limitation for the intestinal damage so far as it is damage appearing in duodenum, small intestine and large intestine and examples thereof include mucosal damage such as erosion and ulcer generated in duodenum, small intestine and large intestine), and symptoms associated with lumbar spinal canal stenosis (e.g., paralysis, dullness in sensory perception, pain, numbness, lowering in walking ability, etc. associated with cervical spinal canal stenosis, thoracic spinal canal stenosis, lumbar spinal canal stenosis, diffuse spinal canal stenosis or sacral stenosis) etc. (see, for example, in WO '084, WO 2009/157396, WO 2009/107736, WO 2009/154246, WO 2009/157397, and WO 2009/157398).

In addition, compound A is useful as an accelerating agent for angiogenic therapy such as gene therapy or autologous bone marrow transplantation, an accelerating agent for angiogenesis in restoration of peripheral artery or angiogenic therapy, etc. (see, for example, in WO '084).

As mentioned above, while the usefulness of compound A as therapeutic agents for the above-mentioned disorders is known, no reference describes or suggests the possibility of existence of crystals of compound A.

BRIEF SUMMARY OF THE INVENTION

A main object of the present invention is to provide a novel crystal of compound A. Additionally, an object of the present invention is to provide a method for producing the crystal, and a pharmaceutical composition containing the crystal as an active ingredient.

It is hoped that medicament bulk is a thing of a high quality for which constant effect can be always shown and of a form which is handled easily industrially. The present inventors have earnestly studied. As a result, the present inventors have found a novel crystal of compound A, and have completed the present invention.

The present invention includes, for example, the following aspects.

One aspect is Form-I crystal of compound A which shows diffraction peaks in the powder X-ray diffraction spectrum of compound A (hereinafter referred to as "Form-I crystal of the invention") at the following angles of diffraction 2θ: 9.4 degrees, 9.8 degrees, 17.2 degrees and 19.4 degrees, wherein the X-ray powder diffraction diagram is obtained by using Cu Kα radiation (λ=1.54 Å), Another aspect is Form-II crystal of compound A which shows diffraction peaks in the powder X-ray diffraction spectrum of compound A (hereinafter referred to as "Form-II crystal of the invention") at the following angles of diffraction 2θ: 9.0 degrees, 12.9 degrees, 20.7 degrees and 22.6 degrees, wherein the X-ray powder diffraction diagram is obtained by using Cu Kα radiation (λ=1.54 Å), Another aspect of the present invention is Form-III crystal of compound A which shows diffraction peaks in the powder X-ray diffraction spectrum of compound A (hereinafter referred to as "Form-III crystal of the invention") at the following angles of diffraction 2θ: 9.3 degrees, 9.7 degrees, 16.8 degrees, 20.6 degrees and 23.5 degrees, wherein the X-ray powder diffraction diagram is obtained by using Cu Kα radiation (λ=1.54 Å)

Yet another aspect of the present invention is a pharmaceutical composition containing the crystal of one of the above three as the active ingredient (hereinafter referred to as "pharmaceutical composition of the invention").

When specifying an angle of diffraction 2 theta (2θ) for a peak in the invention embodiments and the claims, it should be understood that the value given is to be understood as an interval from said value minus 0.2° to said value plus 0.2°, and preferably from said value minus 0.1° to said value plus 0.1°.

DETAILED DESCRIPTION OF THE INVENTION

Figure 1:
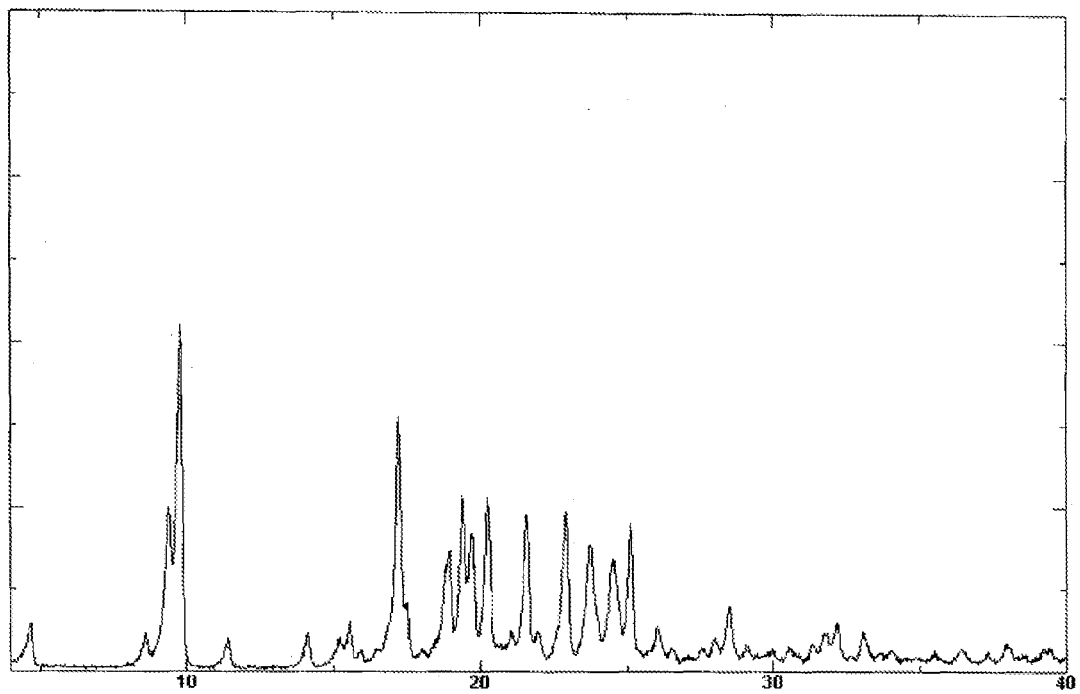
FIG. 1 shows a powder X-ray diffraction spectrum chart of Form-I crystal of the invention. The vertical axis indicates the peak intensity (cps), and the horizontal axis indicates the diffraction angle (2θ[°]).

Form-I crystal of the invention is characterized in that it shows diffraction peaks at 9.4 degrees, 9.8 degrees, 17.2 degrees and 19.4 degrees in the powder X-ray diffraction spectrum of compound A.

Form-II crystal of the invention is characterized in that it shows diffraction peaks at 9.0 degrees, 12.9 degrees, 20.7 degrees and 22.6 degrees in the powder X-ray diffraction spectrum of compound A.

Form-III crystal of the invention is characterized in that it shows diffraction peaks at 9.3 degrees, 9.7 degrees, 16.8 degrees, 20.6 degrees and 23.5 degrees in the powder X-ray diffraction spectrum of compound A.

A. Production of Compound A

Compound A can be produced, for example, according to the method described in WO '084, and, it can also be produced according to the production method mentioned below.

[Formula 2]

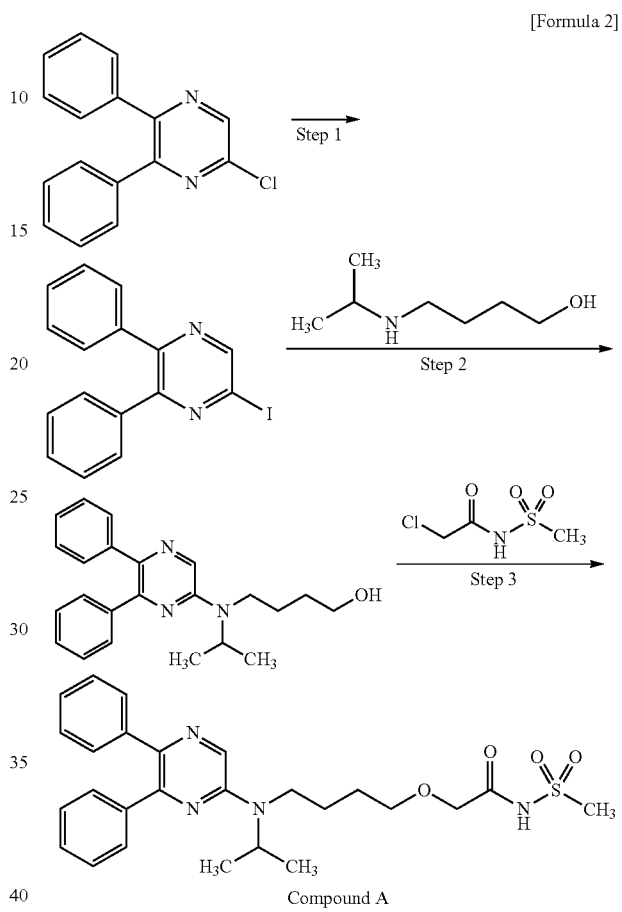

Step 1:
6-Iodo-2,3-diphenylpyrazine can be produced from 6-chloro-2,3-diphenylpyrazine by reacting it with sodium iodide. The reaction is carried out in the presence of an acid in an organic solvent (e.g., ethyl acetate, acetonitrile, acetone, methyl ethyl ketone, or their mixed solvent). The acid to be used is, for example, acetic acid, sulfuric acid, or their mixed acid. The amount of sodium iodide to be used is generally within a range of from 1 to 10 molar ratio relative to 6-chloro-2,3-diphenylpyrazine, preferably within a range of from 2 to 3 molar ratio. The reaction temperature varies depending on the kinds of the solvent and the acid to be used, but may be generally within a range of from 60° C. to 90° C. The reaction time varies depending on the kinds of the solvent and the acid to be used and on the reaction temperature, but may be generally within a range of from 9 hours to 15 hours.

Step 2:
5,6-Diphenyl-2-[4-hydroxybutyl(isopropyl)amino]pyrazine can be produced from 6-iodo-2,3-diphenylpyrazine by reacting it with 4-hydroxybutyl(isopropyl)amine. The reaction is carried out in the presence of a base in an organic solvent (e.g., sulfolane, N-methylpyrrolidone, N,N-dimethylimidazolidinone, dimethyl sulfoxide or their mixed solvent). The base to be used is, for example, sodium hydrogencarbonate, potassium hydrogencarbonate, potassium carbonate, sodium carbonate or their mixed base. The amount of 4-hydroxybutyl(isopropyl)amine to be used may be generally within a range of from 1.5 to 5.0 molar ratio relative to 6-iodo-2,3-diphenylpyrazine, preferably within a range of from 2 to 3 molar ratio. The reaction temperature varies depending on the kinds of the solvent and the base to be used, but may be generally within a range of from 170° C. to 200° C. The reaction time varies depending on the kinds of the solvent and the base to be used and on the reaction temperature, but may be generally within a range of from 5 hours to 9 hours.

Step 3:

Compound A can be produced from 5,6-diphenyl-2-[4-hydroxybutyl(isopropyl)amino]pyrazine by reacting it with N-(2-chloroacetyl)methanesulfonamide. The reaction is carried out in the presence of a base in a solvent (N-methylpyrrolidone, 2-methyl-2-propanol or their mixed solvent). The base to be used is, for example, potassium t-butoxide, sodium t-butoxide or their mixed base. The amount of N-(2-chloroacetyl)methanesulfonamide to be used may be generally within a range of from 2 to 4 molar ratio relative to 5,6-diphenyl-2-[4-hydroxybutyl(isopropyl)amino]pyrazine, preferably within a range of from 2 to 3 molar ratio. The reaction temperature varies depending on the kinds of the solvent and the base to be used, but may be generally within a range of from −20° C. to 20° C. The reaction time varies depending on the kinds of the solvent and the base to be used and on the reaction temperature, but may be generally within a range of from 0.5 hours to 2 hours.

The compounds to be used as the starting materials in the above-mentioned production method for compound A are known compounds, or can be produced by known methods.

B. Productions of Form-I Crystal of the Invention, Form-II Crystal of the Invention, and Form-III Crystal of the Invention (Hereinafter Collectively Referred to as "the Crystals of the Invention")

(I) Production of Form-I Crystal of the Invention

Form-I crystal of the invention can be produced, for example, according to the method described below.

(1) Dissolution Step

This step is a step of dissolving compound A in a solvent by heating. The suitable solvent to be used in the step is, for example, alcoholic solvent, a mixed solvent of alcoholic solvent and ketone solvent. The suitable alcoholic solvent to be used in the step is, for example, methanol, ethanol, 2-propanol, preferably ethanol. The suitable ketone solvent to be used in the step is, for example, methylethylketone.

Especially, the preferable solvent to be used in the step is ethanol or a mixed solvent of ethanol and methylethylketone. In case of a mixed solvent of ethanol and methylethylketone, ethanol is within a range of from 1.5-fold (v/v) to 100-fold (v/v) relative to the amount of methylethylketone, preferably within a range of from 3-fold (v/v) to 50-fold (v/v), more preferably within a range of from 6-fold (v/v) to 20-fold (v/v).

The total volume of the solvent to be used in the step is preferably within a range of from 2-fold (mL/g) to 30-fold (mL/g) relative to the amount of compound A, more preferably within a range of from 3-fold (mL/g) to 20-fold (mL/g), further more preferably within a range of from 4-fold (mL/g) to 15-fold (mL/g). The heating temperature varies depending on the kind of solvent and the volume of the solvent used, but generally is lower than the boiling point of the solvent to be used, and is preferably within a range of from 60° C. to 100° C., more preferably within a range of from 70° C. to 90° C.

In the step, the solution may be filtered to remove insolubles, if necessary. To prevent the precipitation of crystals during the filtration, the filtration is preferably carried out under pressure using a funnel equipped with a heating device. In case the precipitation of crystals is observed in the filtrate, the precipitate is preferably dissolved again by reheating after the filtration.

(2) Cooling Step

This step is a step of precipitating Form-I crystal of the invention from the solution prepared in the above step (1) by cooling. The step is preferably carried out by using a crystallizer equipped with a heating function and a stirring function.

The cooling temperature (temperature when precipitated crystal is collected) is, suitably, within a range of from −10° C. to 50° C., preferably within a range of from 0° C. to 20° C., and more preferably within a range of from 0° C. to 10° C. The step is preferably carried out by cooling within a range of from 3 hours to 95 hours slowly until reaching the cooling temperature.

Additionally, in the step, a seed of Form-I crystal of the invention may be added. In that case, it is preferable that the seed of Form-I crystal of the invention is added when the solution is cooled to a temperature within a range of from 60° C. to 90° C. The amount of the seed crystal of Form-I crystal of the invention is preferably within a range of from 1% to 10% by weight relative to the amount of compound A.

(3) Crystal Collection and Drying Step

This step is a step of collecting the precipitated crystal obtained in the above step (2) using a known means such as filtration and centrifugation, and drying the collected crystal.

A drying step can be carried out by a conventional method such as drying under reduced pressure and over a desiccant. Drying is preferably carried out under reduced pressure (e.g., 10 mmHg or less) at within a range of from 20° C. to 70° C. for one hour to 48 hours.

Additionally, following the above step (1), after partially precipitating crystal by removing the solvent while heating and stirring the solution prepared in the above step (1), Form-I crystal of the invention can be obtained by carrying out the above steps (2) and (3). In the step of removing the solvent, the seed of Form-I crystal of the invention may be added. The amount of the seed of Form-I crystal of the invention is preferably within a range of from 0.1% to 10% by weight relative to the amount of compound A used in the above step (1).

(II) Production of Form-II Crystal of the Invention

Form-II crystal of the invention can be produced, for example, according to the method described below.

(1) Dissolution Step

This step is a step of dissolving compound A in a solvent by heating. The suitable solvent to be used in the step is, for example, alcoholic solvent, ketone solvent, a saturated hydrocarbon solvent, ether solvent, and water, or a mixed solvent thereof. The preferable mixed solvent is a mixture of ether solvent and a saturated hydrocarbon solvent or water, or a mixture of alcohol solvent and ketone solvent or water.

The alcoholic solvent to be used in the step is, for example, a straight or branched alcohol having one to 8 carbon atoms. Specifically, the alcohol solvent may include methanol, ethanol, n-propanol, isopropanol, 1-butanol, 2-butanol, t-butanol, 1-amylalcohol, 1-hexanol, 1-heptanol, 1-octanol. The ether solvent to be used in the step may include tetrahydrofuran, 1,4-dioxane. The saturated hydrocarbon solvent to be used in the step is, for example, a straight or branched alkane having 6 to 8 carbon atoms, or a cycloalkane having 6 to 8 carbon atoms. Specifically, the saturated hydrocarbon solvent may include heptane, octane, cyclohexane, cycloheptane, cyclooctane. The ketone solvent to be used in the step is, for example, a straight or branched one having 3 to 8 carbon atoms. Specifically, the ketone solvent may include acetone, methylethylketone.

The total volume of the solvent to be used in the step is suitably within a range of from 2-fold (mL/g) to 20-fold (mL/g) relative to the amount of compound A, preferably within a range of from 3-fold (mL/g) to 15-fold (mL/g), more preferably within a range of from 5-fold (mL/g) to 10-fold (mL/g). The heating temperature varies depending on the kind of solvent and the volume of the solvent used, but generally is lower than the boiling point of the solvent to be used, and is preferably within a range of from 60° C. to 90° C., more preferably within a range of from 70° C. to 80° C.

In the step, the solution may be filtered to remove insolubles, if necessary. To prevent the precipitation of crystals during the filtration, the filtration is preferably carried out under pressure using a funnel equipped with a heating device. In case the precipitation of crystals is observed in the filtrate, the precipitate is preferably dissolved again by reheating after the filtration.

(2) Cooling Step

This step is a step of precipitating Form-II crystal of the invention from the solution prepared in the above step (1) by cooling. The step is preferably carried out by using a crystallizer equipped with a heating function and a stirring function.

The cooling temperature (temperature when precipitated crystal is collected) is suitably within a range of from −10° C. to 50° C., preferably within a range of from 0° C. to 20° C., and more preferably within a range of from 0° C. to 10° C.

Additionally, in the step, a seed of Form-II crystal of the invention may be added. The amount of the seed of Form-II crystal of the invention is preferably within a range of from 1% to 10% by weight relative to the amount of compound A.

In case Form-II crystal of the invention is produced by using alcoholic solvent or a mixture of alcoholic solvent and ketone solvent as a solvent, it is necessary that the seed of Form-II crystal of the invention be added in the solution prepared in the above step (1) and the solution be cooled, or the solution prepared in the above step (1) be cooled rapidly. The cooling rate is suitably within a range of from 60° C./hour to 600° C./hour.

(3) Crystal Collection and Drying Step

This step is the same as the method described above in "(3) Crystal collection and drying step" in the above-mentioned "(I) Production of Form-I Crystal of the Invention."

(III) Production of Form-III Crystal of the Invention

Form-III crystal of the invention can be produced, for example, according to the method described below.

(1) Dissolution Step

This step is a step of dissolving compound A in a solvent by heating. The suitable solvent to be used in the step is, for example, ester solvent, aromatic hydrocarbon solvent. The suitable ester solvent to be used in the step is, for example, diethylcarbonate, n-butyl acetate, isoamyl acetate, n-amyl acetate, preferably n-butyl acetate. The suitable aromatic hydrocarbon solvent to be used in the step is, for example, ethylbenzene.

The total volume of the solvent to be used in the step is suitably within a range of from 5-fold (mL/g) to 30-fold (mL/g) relative to the amount of compound A, preferably within a range of from 7-fold (mL/g) to 20-fold (mL/g), more preferably within a range of from 10-fold (mL/g) to 15-fold (mL/g). The heating temperature varies depending on the kind of solvent and the volume of the solvent used, but generally is lower than the boiling point of the solvent to be used, preferably within a range of from 40° C. to 90° C., and more preferably within a range of from 50° C. to 80° C.

In the step, the solution may be filtered to remove insolubles, if necessary. To prevent the precipitation of crystals during the filtration, the filtration is preferably carried out under pressure using a funnel equipped with a heating device. In case the precipitation of crystals is observed in the filtrate, the precipitate is preferably dissolved again by reheating after the filtration.

(2) Cooling Step

This step is a step of precipitating Form-III crystal of the invention from the solution prepared in the above step (1) by cooling. The step is preferably carried out using a crystallizer equipped with a heating function and a stirring function.

The cooling rate is suitably within a range of from 0.5° C./hour to 120° C./hour. The cooling temperature (temperature when precipitated crystal is collected) is suitably within a range of from −10° C. to 30° C., preferably within a range of from 0° C. to 20° C., and more preferably within a range of from 0° C. to 10° C.

(3) Crystal Collection and Drying Step

The step is the same as the method described above in "(3) Crystal collection and drying step" in the above-mentioned "(I) Production of Form-I Crystal of the Invention."

C. Medical Use and Pharmaceutical Composition of the Invention

Compound A according to the present invention has an excellent PGI2 agonistic effect and shows a platelet aggregation inhibitory effect, a vasodilative effect, a bronchodilative effect, a lipid deposition inhibitory effect, a leukocyte activation inhibitory effect, etc.

Therefore, the crystals of the invention or the pharmaceutical composition of the invention is useful as preventive or therapeutic agents for transient ischemic attack (TIA), diabetic neuropathy, diabetic gangrene, peripheral circulatory disturbance (e.g., chronic arterial occlusion, intermittent claudication, peripheral embolism, vibration syndrome, Raynaud's disease), connective tissue disease (e.g., systemic lupus erythematosus, scleroderma, mixed connective tissue disease, vasculitic syndrome), reocclusion/restenosis after percutaneous transluminal coronary angioplasty (PTCA), arteriosclerosis, thrombosis (e.g., acute-phase cerebral thrombosis, pulmonary embolism), hypertension, pulmonary hypertension, ischemic disorder (e.g., cerebral infarction, myocardial infarction), angina (e.g., stable angina, unstable angina), glomerulonephritis, diabetic nephropathy, chronic renal failure, allergy, bronchial asthma, ulcer, pressure ulcer (bedsore), restenosis after coronary intervention such as atherectomy and stent implantation, thrombocytopenia by dialysis, the diseases in which fibrosis of organs or tissues is involved [e.g., renal diseases (e.g., tuburointerstitial nephritis), respiratory diseases (e.g., interstitial pneumonia (pulmonary fibrosis), chronic obstructive pulmonary disease), digestive diseases (e.g., hepatocirrhosis, viral hepatitis, chronic pancreatitis and scirrhous stomachic cancer), cardiovascular diseases (e.g, myocardial fibrosis), bone and articular diseases (e.g, bone marrow fibrosis and rheumatoid arthritis), skin diseases (e.g, cicatrix after operation, scalded cicatrix, keloid, and hypertrophic cicatrix), obstetric diseases (e.g., hysteromyoma), urinary diseases (e.g., prostatic hypertrophy), other diseases (e.g., Alzheimer's disease, sclerosing peritonitis, type I diabetes and organ adhesion after operation)], erectile dysfunction (e.g., diabetic erectile dysfunction, psychogenic erectile dysfunction, psychotic erectile dysfunction, erectile dysfunction associated with chronic renal failure, erectile dysfunction after intrapelvic operation for removing prostata, and vascular erectile dysfunction associated with aging and arteriosclerosis), inflammatory bowel disease (e.g., ulcerative colitis, Crohn's disease, intestinal tuberculosis, ischemic colitis and intestinal ulcer associated with Behcet disease), gastritis, gastric ulcer, ischemic ophthalmopathy (e.g., retinal artery occlusion, retinal vein occlusion, ischemic optic neuropathy), sudden hearing loss, avascular necrosis of bone, intestinal damage caused by administration of a non-steroidal anti-inflammatory agent (e.g., diclofenac, meloxicam, oxaprozin, nabumetone, indomethacin, ibuprofen, ketoprofen, naproxen, celecoxib) (there is no particular limitation for the intestinal damage so far as it is damage appearing in duodenum, small intestine and large intestine and examples thereof include mucosal damage such as erosion and ulcer generated in duodenum, small intestine and large intestine), and symptoms associated with lumbar spinal canal stenosis (e.g., paralysis, dullness in sensory perception, pain, numbness, lowering in walking ability, etc. associated with cervical spinal canal stenosis, thoracic spinal canal stenosis, lumbar spinal canal stenosis, diffuse spinal canal stenosis or sacral stenosis) etc. In addition, the crystals of the invention or the pharmaceutical composition of the invention is also useful as an accelerating agent for angiogenic therapy in gene therapy or autologous bone marrow transplantation, an accelerating agent for angiogenesis in restoration of peripheral artery or angiogenic therapy, etc. If the crystals of the invention are administered as a medicine, the pharmaceutical composition of the invention is the crystals of the invention as it is or contains the crystals of the invention in a pharmaceutically acceptable, nontoxic and inert carrier within a range of from 0.1% to 99.5%, preferably within a range of from 0.5% to 90%.

Examples of the carrier include solid, semi-solid or liquid diluent, filler and other auxiliary agents for pharmaceutical formulation. These can be used alone or as a mixture of two or more thereof.

The pharmaceutical composition of the invention may be in any of the forms of oral preparations such as powder, capsules, tablets, sugar-coated tablets, granules, diluted powder, suspension, liquid, syrup, elixir or troche, and parenteral preparations such as injection or suppository in a solid or liquid dose unit. It may also be in a form of a sustained release preparation. Among them, oral preparations such as tablets are particularly preferred.

Powder is able to be manufactured by making the crystals of the invention into an appropriate fine size.

Diluted powder is able to be manufactured by such a manner that the crystals of the invention are made into an appropriate fine size and then mixed with a pharmaceutical carrier which is similarly made into a fine size such as edible carbohydrate (e.g., starch and mannitol). Flavoring agent, preservative, dispersing agent, coloring agent, perfume, etc. may be optionally added thereto.

Capsules are able to be manufactured by such a manner that the powder or diluted powder which is made powdery as mentioned above or granules which will be mentioned under the item for tablets are filled in an capsule shell such as gelatin capsule. It is also possible to manufacture in such a manner that the powder or the diluted powder in a powdery form is mixed with a lubricant or a fluidizing agent such as colloidal silica, talc, magnesium stearate, calcium stearate or solid polyethylene glycol followed by subjecting it to a filling operation. When a disintegrating agent or solubilizing agent such as carboxymethyl cellulose, carboxymethyl cellulose calcium, lowly-substituted hydroxypropyl cellulose, croscarmellose sodium, carboxymethyl starch sodium, calcium carbonate or sodium carbonate is added, efficacy of the pharmaceutical when the capsules are ingested can be improved. It is also possible that fine powder of the crystals of the invention is suspended/dispersed in vegetable oil, polyethylene glycol, glycerol or surfactant and wrapped with a gelatin sheet to give a soft capsule preparation.

Tablets are able to be manufactured in such a manner that a powdery mixture is prepared by addition of a filler to the crystals of the invention which have been made powdery and made into granules or slugs and then a disintegrating agent or a lubricant is added thereto followed by making them into tablets.

The powdery mixture is able to be manufactured by mixing appropriately powdered crystals of the invention with a diluent or a base. If necessary, it is possible to add a binder (such as carboxymethyl cellulose sodium, methyl cellulose, hydroxypropyl methyl cellulose, gelatin, polyvinylpyrrolidone or polyvinyl alcohol), a dissolution retarding agent (such as paraffin), a reabsorbing agent (such as a quaternary salt), an adsorbent (such as bentonite or kaolin), etc. thereto.

The powdery mixture is able to be made into granules in such a manner that it is firstly made wet by using a binder, for example, syrup, starch paste, acacia, cellulose solution or polymer solution, mixed with stirring and dried followed by grinding. Instead of making the powder into granules as such, it is also possible that the powder is applied to a tabletting machine and the resulting slug in an incomplete shape is ground to give granules. When a lubricant such as stearic acid, stearate, talc or mineral oil is added to the granules prepared as such, sticking of the granules to each other can be prevented.

Tablets are also able to be manufactured in such a manner that the crystals of the invention are mixed with a fluid inert carrier and then directly making them into tablets without conducting the above steps of making them into granules or slugs.

The tablets prepared as such can be subjected to film coating or sugar coating. It is also possible to apply a transparent or semi-transparent protective coat made of a tightly closed shellac film, a coat made of sugar or polymer material, or a polished coat made of wax.

In other oral preparations such as liquid, syrup, troche or elixir, it is also possible to make it into a dose unit form wherein a predetermined amount thereof contains a predetermined amount of the crystal of the present invention.

The syrup is able to be manufactured by dissolving the crystals of the invention into an appropriate aqueous solution of a flavor. The elixir is able to be manufactured by using a non-toxic alcoholic carrier.

The suspension is able to be manufactured by dispersing the crystals of the invention into a non-toxic carrier. If necessary, it is possible to add a solubilizing agent or an emulsifier (such as ethoxylated isostearyl alcohol and polyoxyethylene sorbitol ester), a preservative or a flavor-endowing agent (such as peppermint oil or saccharine) thereto.

If necessary, the dose unit formulation for oral administration may be made into microcapsules. The formulation is also able to be coated or embedded into polymer or wax to obtain a prolonged action or sustained release of the active ingredient.

The parenteral preparation may be in a liquid dose unit form for subcutaneous, intramuscular or intravenous injection such as in a form of solution or suspension. The parenteral preparation is able to be manufactured in such a manner that a predetermined amount of the crystals of the invention is suspended or dissolved in a non-toxic liquid carrier meeting the purpose of injection such as aqueous or oily medium and then the suspension or solution is sterilized. Non-toxic salt or a solution thereof may be added thereto for making the injection solution isotonic. It is also possible to add a stabilizer, a preservative, an emulsifier and the like.

The suppository is able to be manufactured by dissolving or suspending the crystals of the invention in a low-melting and water-soluble or insoluble solid such as polyethylene glycol, cacao fat, semi-synthetic fat/oil (such as Witepsol (registered trade mark)), higher ester (such as myristyl palmitate ester) or a mixture thereof.

Although the dose may vary depending upon the state of a patient such as body weight or age, administering route or degree of symptom, a range of from 0.001 mg to 100 mg per day as an amount of the crystals of the invention is generally suitable for an adult and a range of from 0.01 mg to 10 mg is more preferable. In some cases, a dose less than the above may be sufficient or, on the other hand, a dose more than the above may be necessary. It is also possible to administer one to several times a day or to administer with an interval of one to several days.

EXAMPLES

The present invention is described in more detail with reference to Examples and Test Examples given below; however, the present invention should not be limited whatsoever to these Examples.

For the powder X-ray diffractometry, Rigaku Corporation's RINT-Ultima III (target: Cu, voltage: 40 kV, current: 40 mA, scan speed: 4 degrees/min) was used.

Example 1

Production of Form-I Crystal of the Invention

Ethanol (440 ml) was added to compound A (40 g), and the mixture was stirred and heated in an oil bath of 100° C. to 110° C. After compound A was dissolved, ethanol (280 ml) was removed. The obtained concentrate was stirred and heated under reflux in a water bath of 80° C. for 1 hour. The solution was gradually cooled to 10° C. in 20 hours while stirring, and the precipitated crystal was collected through filtration. The obtained crystal was washed with a small amount of ethanol (48 ml), and dried under reduced pressure at 60° C. to give Form-I crystal of the invention (38.93 g, 97.3%). A powder X-ray diffraction spectrum of the Form-I crystal of the invention is shown in FIG. 1.

Mp: 140.4° C. (the Japanese Pharmacopoeia, method 1 of Melting Point Determination)

Example 2

Production of Form-I Crystal of the Invention

Ethanol (99 g) and methylethylketone (11 g) were added to compound A (20 g), and heated at 77° C. to dissolve compound A, and then the solution was gradually cooled to 10° C. in 20 hours. During cooling, to the solution was added a small amount of Form-I crystal of the invention. After cooling, the precipitated crystal was collected through filtration, washed with ethanol, and dried under reduced pressure to give Form-I crystal of the invention (18.72 g, 93.6%).

Example 3

Production of Form-II Crystal of the Invention

Figure 2:
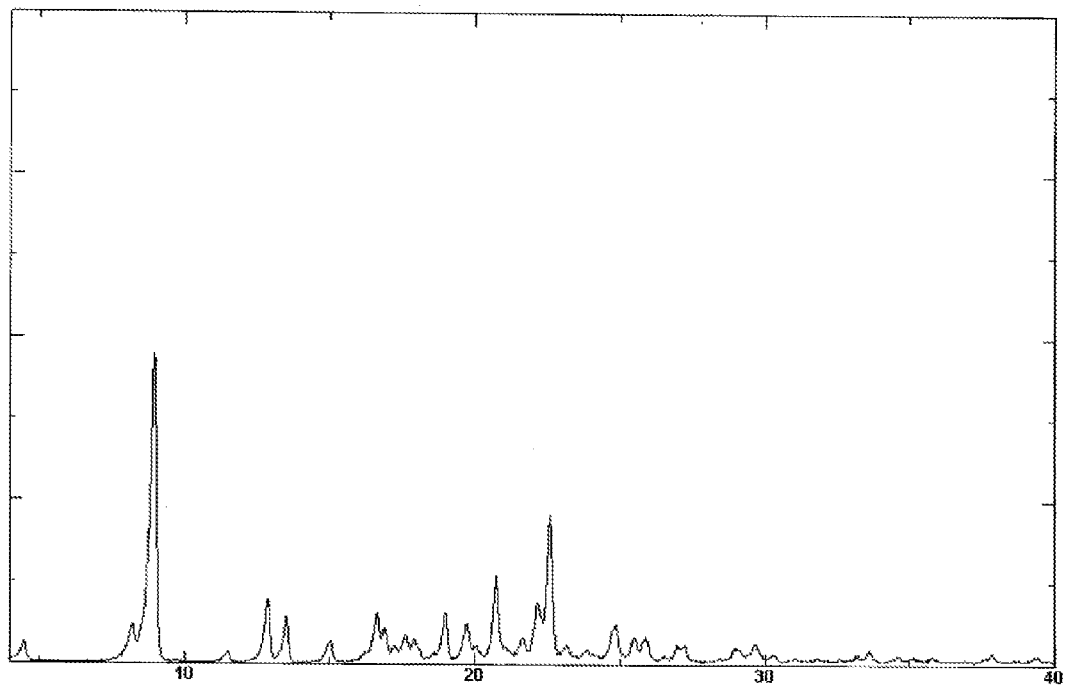
FIG. 2 shows a powder X-ray diffraction spectrum chart of Form-II crystal of the invention. The vertical axis indicates the peak intensity (cps), and the horizontal axis indicates the diffraction angle (2θ[°]).

Ethanol (550 g) and methyl ethyl ketone (55 g) were added to compound A (100 g), heated at 77° C., and filtered under pressure while kept heated. With stirring, the resulting filtrate was cooled from 70° C. to 0° C., taking 30 minutes, and after reaching 0° C., this was stirred at 0° C. for 2.5 hours. The precipitated crystal was collected through filtration, washed with ethanol (200 ml), and dried under reduced pressure. Ethanol (99 g) and methyl ethyl ketone (11 g) were added to the obtained crystal (20 g), heated at 70° C., then kept at 70° C. for 1 hour, and gradually cooled to 10° C., taking 20 hours; and after reaching 10° C., this was stirred at 10° C. for 1 hour. The precipitated crystal was collected through filtration, washed with ethanol (40 ml), and dried under reduced pressure to give Form-II crystal of the invention (18.73 g, 93.7%). A powder X-ray diffraction spectrum of Form-II crystal of the invention is shown in FIG. 2.

Mp: 135.2° C. (the Japanese Pharmacopoeia, method 1 of Melting Point Determination)

Example 4

Production of Form-II Crystal of the Invention

Ethanol (99 g) and methylethylketone (11 g) were added to compound A (20 g), and heated at 77° C. to dissolve compound A, and then the solution was gradually cooled to 10° C. in 20 hours. During cooling, to the solution was added a small amount of Form-II crystal of the invention. After cooling, the precipitated crystal was collected through filtration, washed with ethanol, and dried under reduced pressure to give Form-II crystal of the invention (19.70 g, 98.5%).

Example 5

Production of Form-III Crystal of the Invention

Figure 3:
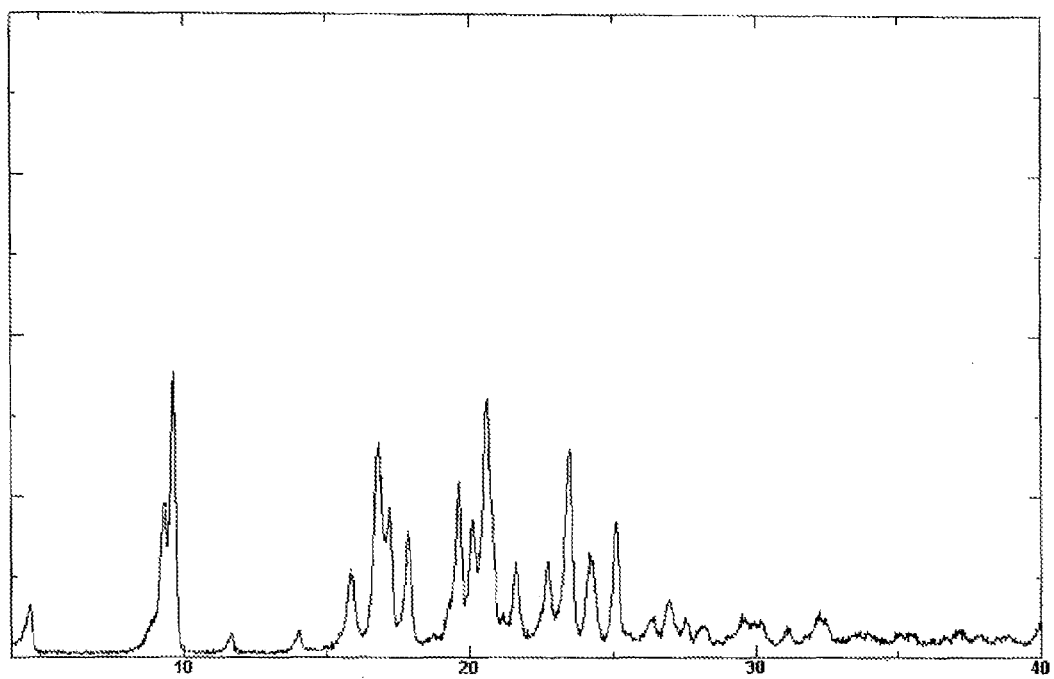
FIG. 3 shows a powder X-ray diffraction spectrum chart of Form-III crystal of the invention. The vertical axis indicates the peak intensity (cps), and the horizontal axis indicates the diffraction angle (2θ[°]).

N-Butyl acetate (500 ml) was added to compound A (36.7 g), and heated at 75° C. to dissolve compound A, and then cooled to 5° C. Then, a process of heating to 60° C. and cooling to 5° C. was carried out, and the process was repeated. The precipitated crystal was collected through filtration, washed with a small amount of isopropyl acetate (50 ml), and dried under reduced pressure to give Form-III crystal of the invention (29.0 g, 79.0%). A powder X-ray diffraction spectrum of Form-III crystal of the invention is shown in FIG. 3.

Mp: 138.0° C. (the Japanese Pharmacopoeia, method 1 of Melting Point Determination)

The crystals of the invention used in the following Test Examples 1 to 3 were prepared by the following method.

Form-I crystal of the invention, Form-II crystal of the invention, and Form-III crystal of the invention were prepared in the same methods as in Example 2, Example 4, and Example 5, respectively.

Test Example 1

Measurement of Particle Size (1) Measurement of Particle Size Distribution of the Crystals of the Invention After a dispersant (10 mL) was added to the crystals of the invention (20 mg) followed by shaking up, the crystals of the invention were dispersed with ultrasonic wave. The particle size distributions of the crystals of the invention were measured by using HORIBA LA-910. The result is shown in Table 1.

The dispersant used is a filtered saturated solution of compound A in 0.1 v/v % Polysorbate 80 aqueous solution.

TABLE 1

| | Crystal Form | D10 | D50 | D90 |
|---|---|---|---|---|
| 1 | Form-I Crystal of the Invention | 5.6 | 12.8 | 25.8 |
| 2 | Form-II Crystal of the Invention | 5.2 | 11.3 | 22.0 |
| 3 | Form-III Crystal of the Invention | 4.3 | 8.0 | 14.4 |

D10: Cumulative undersize particle diameter at 10% of volumetric ratio [μm]
D50: Cumulative undersize particle diameter at 50% of volumetric ratio [μm]
D90: Cumulative undersize particle diameter at 90% of volumetric ratio [μm]

(2) Observation of the Crystals of the Invention with Electron Scanning Microscope The crystals were observed through an electron scanning microscope (HITACHI HIGH TECHNOLOGIES TM-1000 Miniscope).

Figure 4:
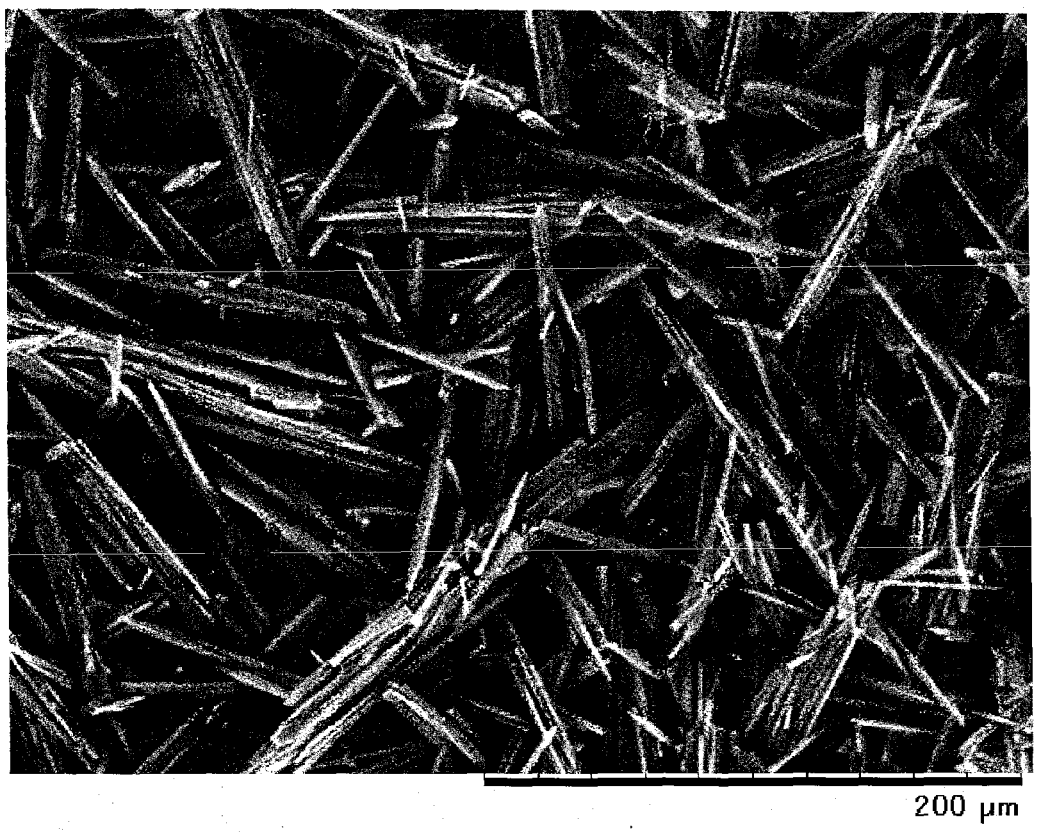
FIG. 4 shows a scanning electron micrograph of Form-I crystal of the invention.
Figure 5:
FIG. 5 shows a scanning electron micrograph of Form-II crystal of the invention.
Figure 6:
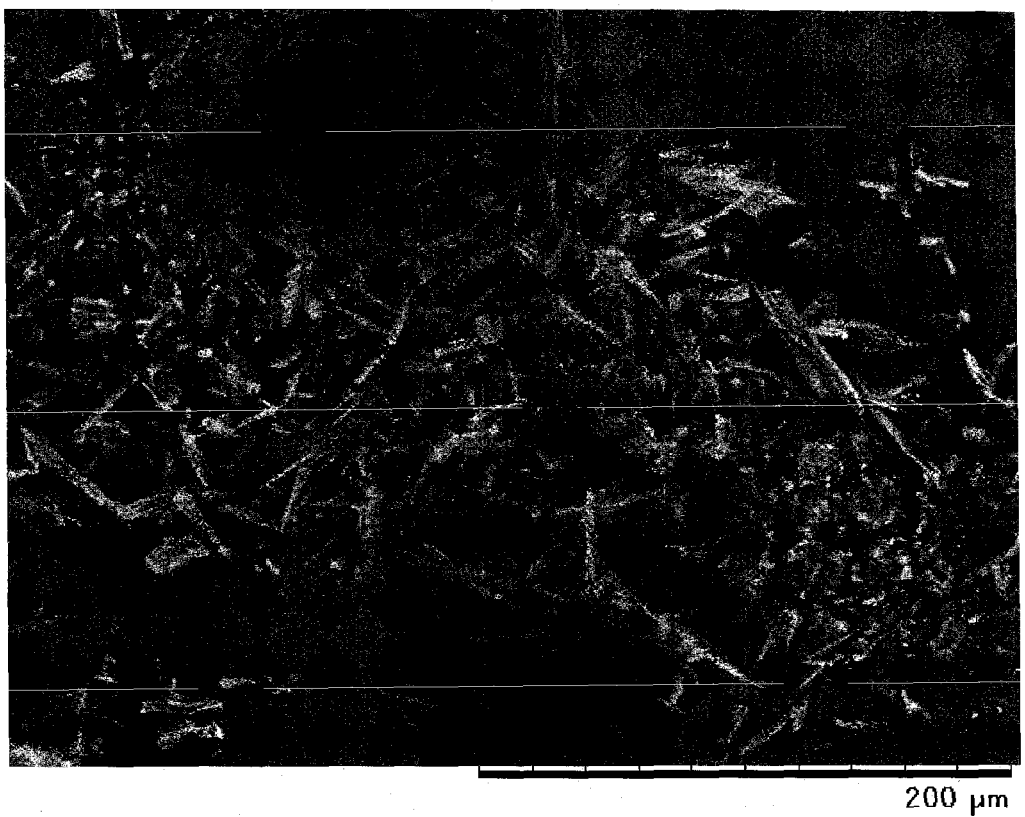
FIG. 6 shows a scanning electron micrograph of Form-III crystal of the invention.

FIG. 4 shows the electron scanning micrograph of Form-I crystal of the invention. FIG. 5 shows that of Form-II crystal and FIG. 6 shows that of Form-III crystal.

From the results of (1) and (2) mentioned above, it was concluded that the particle size of Form-I crystal of the invention is larger than those of Form-II and Form-III crystals.

Test Example 2

Measurement of Residual Solvent Contained in Crystals of the Invention

The concentration of residual solvent contained in the crystals of the invention was measured by using the following measurement conditions. The result is shown in Table 2.
(Measurement Conditions)
GC Apparatus
 Detector: Flame Ionization Detector
 Column: Capillary Column
 Column Temperature: 150° C.-230° C.
 Injection Temperature: 200° C.
 Detector Temperature: 300° C.
 Carrier Gas: Helium

TABLE 2

| | Crystal Form | Solvent | Content (ppm) |
|---|---|---|---|
| 1 | Form-I Crystal of the Invention | Ethanol | 371 |
| | | Methyl-ethyl-ketone | 82 |
| 2 | Form-II Crystal of the Invention | Ethanol | 2169 |
| | | Methyl-ethyl-ketone | 246 |
| 3 | Form-III Crystal of the Invention | Isopropyl acetate | 93 |
| | | n-Butyl acetate | 2781 |

Although each crystal Form did not contain a considerable amount of residual solvents, the amount of the residual solvents in Form-I crystal of the invention was less than those of Form-II and Form-III.

Test Example 3

Impurity-Removing Effect in Recrystallization

The effectiveness of removing impurities in the course of the recrystallization of each crystal form was measured by using the following measurement conditions (reversed-phase liquid chromatography).
(Measurement Conditions)
HPLC Apparatus
 Detector: Ultraviolet Absorption Detector
 Column: ODS Column
 Column Temperature: 40° C.
 Mobile Phase: Mixture of Water, Acetonitrile and Methanesulfonic acid The purity (%) of each crystal of compound A was calculated by the following equation.

Purity(%)=(Peak area of compound $A$)/(Total area)×100

The removal ratio of impurities (%) for each crystal was calculated by the following equation.

Removal ratio of impurities(%)={[(Purity of each crystal of compound $A$)−(Purity of crude compound $A$)]/[100−(Purity of crude compound $A$)]}×100

The result is shown in Table 3.

TABLE 3

| | Crystal Form | Purity of Compound A (%) | Ratio of Impurity Removal (%) |
|---|---|---|---|
| | Crude Material | 98.04 | |
| 1 | Form-I Crystal of the Invention | 99.51 | 75 |
| 2 | Form-II Crystal of the Invention | 99.33 | 66 |
| 3 | Form-III Crystal of the Invention | 98.97 | 47 |

From the result shown in Table 3, the effectiveness of removing impurities for Form-I crystal of the invention was the highest compared with those for Form-II and III crystals.

Test Example 4

Investigation of Solvent for Crystallization of Compound A

Investigations of crystallization of compound A were executed according to the methods of the following (1) and (2).
(1) Crystallization solvent (see Tables 4 and 5) was added to compound A, and the mixture was stirred at 50° C. for 60 minutes. The resulting mixture was filtered. After the filtration, the isolated mother liquor was stirred at 60° C. for 30 minutes, and cooled down to 5° C. over 11 hours. After stirring at 5° C. for 72 hours, the precipitated solid was collected by filtration. The solid was dried at 20° C. under reduced pressure, whereby a solid was obtained.

Powder X-ray diffraction spectrums of the obtained crystals were measured and the form of each crystal was determined.

The results are shown in Table 4 (investigation by single solvents) and Table 5 (investigation by mixed solvents).

In the investigation by mixed solvents (Table 5), each solvent was mixed and used in an equal amount.

TABLE 4

| | Crystallization Solvent | Crystal Form |
|---|---|---|
| 1 | tert-Butyl methyl ether | NA |
| 2 | Acetone | Form-II Crystal of the Invention + Form-III Crystal of the Invention |
| 3 | Chloroform | NA |
| 4 | Methanol | Form-II Crystal of the Invention + Form-III Crystal of the Invention |
| 5 | Tetrahydrofuran | Form-II Crystal of the Invention + Form-III Crystal of the Invention |
| 6 | Isopropyl ether | NA |
| 7 | 2-Methyltetrahydrofuran | Form-II Crystal of the Invention + Form-III Crystal of the Invention |

TABLE 4-continued

| | Crystallization Solvent | Crystal Form |
|---|---|---|
| 8 | Ethanol | NA |
| 9 | Cyclohexane | NA |
| 10 | Acetonitrile | Form-II Crystal of the Invention + Form-III Crystal of the Invention |
| 11 | 1,2-Dichloroethane | NA |
| 12 | Fluorobenzene | Form-II Crystal of the Invention + Form-III Crystal of the Invention |
| 13 | 1,2-Dimethoxyethane | Form-II Crystal of the Invention + Form-III Crystal of the Invention |
| 14 | Methylcyclohexane | NA |
| 15 | Nitromethane | Form-II Crystal of the Invention + Form-III Crystal of the Invention |
| 16 | 1,4-Dioxane | NA |
| 17 | 3,3-Dimethyl-2-butanone | Form-II Crystal of the Invention + Form-III Crystal of the Invention |
| 18 | Isobutanol | NA |
| 19 | Toluene | Form-II Crystal of the Invention + Form-III Crystal of the Invention |
| 20 | Diethylcarbonate | Form-III Crystal of the Invention |
| 21 | n-Butyl acetate | Form-III Crystal of the Invention |
| 22 | Chlorobenzene | Form-II Crystal of the Invention + Form-III Crystal of the Invention |
| 23 | Ethylbenzene | NA |
| 24 | p-Xylene | NA |
| 25 | Isoamyl acetate | Form-III Crystal of the Invention |
| 26 | n-Amyl acetate | Form-III Crystal of the Invention |
| 27 | Methyl-phenyl-ether | Form-II Crystal of the invention + Form-III Crystal of the invention |
| 28 | Cyclohexanone | NA |
| 29 | bis(2-Methoxy ethyl)ether | Form-III Crystal of the invention |
| 30 | 1,3,5-Trimethylbenzene | Amorphous |
| 31 | 4-Hydroxy-4-methyl-2-pentanone | Form-II Crystal of the invention + Form-III Crystal of the invention |
| 32 | 2,6-Dimethyl-4-heptanone | Form-III Crystal of the invention |

NA: Solid was not precipitated.

TABLE 5

| | Crystallization Solvent | Crystal Form |
|---|---|---|
| 1 | Chloroform Acetonitrile | NA |
| 2 | Tetrahydrofuran Cyclohexane | Form-II Crystal of the Invention |
| 3 | Ethyl formate Water | Form-II Crystal of the Invention + Form-III Crystal of the invention |
| 4 | Methanol Water | NA |
| 5 | Acetonitrile Water | Form-II Crystal of the Invention + Form-III Crystal of the Invention |
| 6 | 1,2-Dimethoxyethane Water | Form-II Crystal of the Invention + Form-III Crystal of the Invention |
| 7 | Ethanol Water | Form-II Crystal of the Invention |
| 8 | Cyclohexane 1,4-Dioxane | Form-II Crystal of the Invention |
| 9 | 2-Propanol Water | Form-II Crystal of the Invention |
| 10 | Cyclohexanone Tetrahydrofuran | NA |
| 11 | 1-Propanol Water | Form-II Crystal of the Invention |
| 12 | 1,4-Dioxane Water | Form-II Crystal of the Invention |
| 13 | 2-Butanol Water | Form-II Crystal of the Invention |
| 14 | Cyclohexanone Cyclohexane | Form-II Crystal of the Invention + Form-III Crystal of the Invention |
| 15 | 1-Butanol Water | Form-II Crystal of the Invention |
| 16 | Cyclohexanone 1,4-Dioxane | Form-II Crystal of the Invention + Form-III Crystal of the Invention |

NA: Solid was not precipitated.

(2) Further investigations were executed using the following method for those conditions under which crystals were not precipitated (see Tables 4 and 5) and conditions similar to them. The solvents used in the further experiments were selected in consideration of toxicity, solubility of compound A and availability for industrial use.

An amount of solvent less than that of the test in the above-mentioned (1) was added to compound A, and the mixture was heated to 75° C. with stirring. After dissolving compound A, the mixture was stirred at 65° C. for 5 to 8 hours. The mixture was cooled down to 20° C. over 9 hours. The precipitated crystal was collected by filtration and dried at 70° C. under reduced pressure, whereby a crystal was obtained. The results are shown in Table 6.

In the investigation by mixed solvents, each solvent was mixed and used in an equal amount.

TABLE 6

| | Crystallization Solvent | Crystal Form |
|---|---|---|
| 1 | tert-Butyl methyl ether | NA |
| 2 | Isopropyl ether | NA |
| 3 | Cyclohexane | NA |
| 4 | Ethanol | Form-I Crystal of the Invention |
| 5 | 2-Propanol | Form-I Crystal of the Invention + Form-III Crystal of the Invention |
| 6 | Ethylbenzene | Form-III Crystal of the Invention |
| 7 | Methanol Water | Form-I Crystal of the Invention + Form-III Crystal of the Invention |
| 8 | Cyclohexanone Tetrahydrofuran | NA |

NA: Solid was not precipitated.

From the results of the above-mentioned (1) and (2), it was concluded that Form-II crystal of the invention and Form-III crystal of the invention can be obtained from various solvents.

On the other hand, crystals which contain Form-I crystal of the invention could be obtained only from alcohol solvents, and highly pure Form-I crystal of the invention could be obtained from ethanol.

What is claimed is:

1. A crystal of 2-{4-[N-(5,6-diphenylpyrazin-2-yl)-N-isopropylamino]butyloxy}-N-(methylsulfonyl)acetamide, showing diffraction peaks in its X-ray powder diffraction spectrum at least at the following angles of diffraction 2θ: 9.0 degrees, 12.9 degrees, 20.7 degrees and 22.6 degrees, wherein the X-ray powder diffraction diagram is obtained by using Cu Kα radiation.

2. A pharmaceutical composition comprising the crystal of claim 1 as an active ingredient.

3. A method for treating diabetic neuropathy, diabetic gangrene, peripheral circulatory disturbance, chronic arterial occlusion, intermittent claudication, scleroderma, thrombosis, pulmonary hypertension, myocardial infarction, angina, glomerulonephritis, diabetic nephropathy, chronic renal failure, bronchial asthma, interstitial pneumonia (pulmonary fibrosis), chronic obstructive pulmonary disease, inflammatory bowel disease, or symptoms associated with spinal canal stenosis, comprising the step of administering the crystal of claim 1 as an active ingredient to a subject.

4. The method according to claim 3, wherein the method is for treating peripheral circulatory disturbance.

5. The method according to claim 3, wherein the method is for treating chronic arterial occlusion.

6. The method according to claim 3, wherein the method is for treating intermittent claudication.

7. The method according to claim 3, wherein the method is for treating scleroderma.

8. The method according to claim 3, wherein the method is for treating pulmonary hypertension.

9. The method according to claim 3, wherein the method is for treating pulmonary fibrosis.

10. The method according to claim 3, wherein the method is for treating symptoms associated with spinal canal stenosis.

11. The method according to claim 3, wherein the method is for treating chronic renal failure.

* * * * *